US009592145B2

United States Patent
Garrec

(10) Patent No.: US 9,592,145 B2
(45) Date of Patent: Mar. 14, 2017

(54) SHOULDER MECHANISM FOR ORTHESIS

(75) Inventor: Philippe Garrec, Gif sur Yvette (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 1282 days.

(21) Appl. No.: 13/395,184

(22) PCT Filed: Sep. 6, 2010

(86) PCT No.: PCT/EP2010/005452
§ 371 (c)(1),
(2), (4) Date: Mar. 9, 2012

(87) PCT Pub. No.: WO2011/029564
PCT Pub. Date: Mar. 17, 2011

(65) Prior Publication Data
US 2012/0172769 A1 Jul. 5, 2012

(30) Foreign Application Priority Data
Sep. 9, 2009 (FR) ..................................... 09 04313

(51) Int. Cl.
A61H 1/02 (2006.01)
A61F 5/01 (2006.01)
B25J 9/00 (2006.01)

(52) U.S. Cl.
CPC ............. A61F 5/013 (2013.01); B25J 9/0006 (2013.01); *A61H 1/0274* (2013.01)

(58) Field of Classification Search
CPC ...... A61H 1/02; A61H 1/0274; A61H 1/0281; A61H 2205/06; A61H 2201/1635; A61F 5/013; B25J 9/0006

(Continued)

(56) References Cited

U.S. PATENT DOCUMENTS 3,449,769 A * 6/1969 Mizen ..................... A61F 2/54
601/23
4,669,451 A 6/1987 Blauth et al.
(Continued)

FOREIGN PATENT DOCUMENTS

DE 199 40 603 A1 4/2001
FR 2 917 323 A1 12/2008
(Continued)

OTHER PUBLICATIONS

International Search Report of PCT/EP2010/005452 dated Mar. 31, 2011.

*Primary Examiner* — Justine Yu
*Assistant Examiner* — Christopher Miller
(74) *Attorney, Agent, or Firm* — Sughrue Mion, PLLC

(57) ABSTRACT

The invention relates to a shoulder mechanism for an orthosis comprising in succession:
 a first element (1) that is stationary relative to the user;
 a second element (2) that is hinged to the first element about a first hinge axis (A1);
 a third element (3) that is hinged to the second element about a second hinge axis (A2); and
 an upper arm (4) that is hinged to the third element about a third hinge axis (A3).

According to the invention, the hinge axes (A1, A2, A3) extend in directions that define a frame of reference that is non-orthogonal.

5 Claims, 3 Drawing Sheets

(58) Field of Classification Search
USPC .......................................................... 602/20
See application file for complete search history.

(56) References Cited

U.S. PATENT DOCUMENTS

| | | | | |
|---|---|---|---|---|
| 5,407,420 A * | 4/1995 | Bastyr | ................. | A61F 5/05858 |
| | | | | 602/16 |
| 5,417,643 A * | 5/1995 | Taylor | ................. | A61H 1/0274 |
| | | | | 601/24 |
| 5,845,540 A * | 12/1998 | Rosheim | .................... | B25J 3/04 |
| | | | | 414/4 |
| 6,155,993 A * | 12/2000 | Scott | .................... | A61B 5/4528 |
| | | | | 600/595 |
| 6,301,526 B1 * | 10/2001 | Kim | ...................... | B25J 9/0006 |
| | | | | 600/1 |
| 8,347,710 B2 * | 1/2013 | Scott | ................... | A61B 5/1038 |
| | | | | 414/2 |
| 2003/0115954 A1 * | 6/2003 | Zemlyakov | ............ | A61B 5/022 |
| | | | | 73/379.01 |
| 2006/0150753 A1 * | 7/2006 | Massimo | ............... | B25J 9/0006 |
| | | | | 73/865.4 |
| 2007/0225620 A1 * | 9/2007 | Carignan | ............. | A61H 1/0281 |
| | | | | 601/5 |
| 2008/0009771 A1 | 1/2008 | Perry et al. | | |
| 2009/0281465 A1 * | 11/2009 | Fu | ........................ | A61H 1/0274 |
| | | | | 601/5 |
| 2010/0145238 A1 * | 6/2010 | Stienen | .............. | A63B 21/1403 |
| | | | | 601/33 |
| 2011/0251533 A1 * | 10/2011 | Han | ..................... | A61H 1/0274 |
| | | | | 601/33 |

FOREIGN PATENT DOCUMENTS

WO      WO 95/32842 A2    12/1995
WO    WO 2008/031023 A2    3/2008

\* cited by examiner

SHOULDER MECHANISM FOR ORTHESIS

CROSS REFERENCE TO RELATED APPLICATIONS

This application is a National Stage of International Application No. PCT/EP2010/005452 filed Sep. 6, 2010, claiming priority based on French Patent Application No. 09 04313 filed Sep. 9, 2009, the contents of all of which are incorporated herein by reference in their entirety.

The invention relates to a shoulder mechanism for an orthosis.

TECHNOLOGICAL BACKGROUND OF THE INVENTION

Shoulder mechanisms are known that include a first element that is secured to the user of the mechanism. The first element may be stationary, or worn by the user. A second element is hinged to the first element about a first hinge axis that is substantially horizontal, extending in a longitudinal direction that extends from front to back relative to the user. A third element is hinged to the second element about a second hinge axis that is substantially vertical when the mechanism is at rest (i.e. when the user's arm extends down along the user's body), the second hinge axis being perpendicular to the first hinge axis. Finally, the upper arm proper of the mechanism is hinged to the third element about a third hinge axis that is once more substantially horizontal, and that is substantially perpendicular to the first and second hinge axes.

Shoulder mechanisms are known in which the three hinges are made by means of successive pivots. Nevertheless, such mechanisms generally present interference with the user's arm while the arm is being moved. In particular, the second pivot, i.e. the pivot constituting the hinge of the third element on the second element, is carried by the second element so as to extend above the shoulder, such that when performing an abduction movement of the arm, the second pivot comes very quickly into the vicinity of the user's head, thereby greatly limiting the permissible amplitude of the abduction movement.

Proposals have been made to provide the hinge between the third element and the second element by means of a slideway that extends along a circular arc, the arc extending horizontally at rest so as to go around the user's shoulder. Such an arrangement presents numerous advantages, in particular the advantage of minimizing interference between the mechanism and the user during ordinary movements of the arm.

Nevertheless, such an arrangement can present certain drawbacks. An abduction movement of the user through angles close to 90 degrees brings the slideway into the vicinity of the user's face, and that can be troublesome. Furthermore, for practical reasons of implementation, it is difficult for the radius of the slideway to be made smaller than 100 millimeters, which prevents making orthosis mechanisms that are suitable for children. Furthermore, the slideway is subjected to large amounts of bending, which can lead to mechanical weakness, and also to an increase in friction.

OBJECT OF THE INVENTION

An object of the invention is to propose an orthosis mechanism that avoids using a circularly arcuate slideway, while still allowing angular movements of large amplitude.

BRIEF SUMMARY OF THE INVENTION

In order to achieve this object, the invention provides a shoulder mechanism for an orthosis comprising in succession:
a first element that is stationary relative to the user;
a second element that is hinged to the first element about a first hinge axis;
a third element that is hinged to the second element about a second hinge axis; and
an upper arm that is hinged to the third element about a third hinge axis.

According to the invention, the hinge axes extend in directions that define a frame of reference that is non-orthogonal.

Such an arrangement minimizes any risk of interference with the user, and makes it possible once more to use bearings when making the hinges. This arrangement also enables the hinge elements to move through greater angles, thereby making a greater working volume available. As with other mechanisms, it is appropriate to avoid any singularity as occurs when two of the hinge axes of the mechanism come into alignment.

Preferably, the hinge axes are inclined relative to the vertical and horizontal directions when the user's arm is at rest.

DESCRIPTION OF THE FIGURES

The invention can be better understood in the light of the following description of the figures in the accompanying drawings, in which.

DETAILED DESCRIPTION OF THE FIGURES

Figure 1:
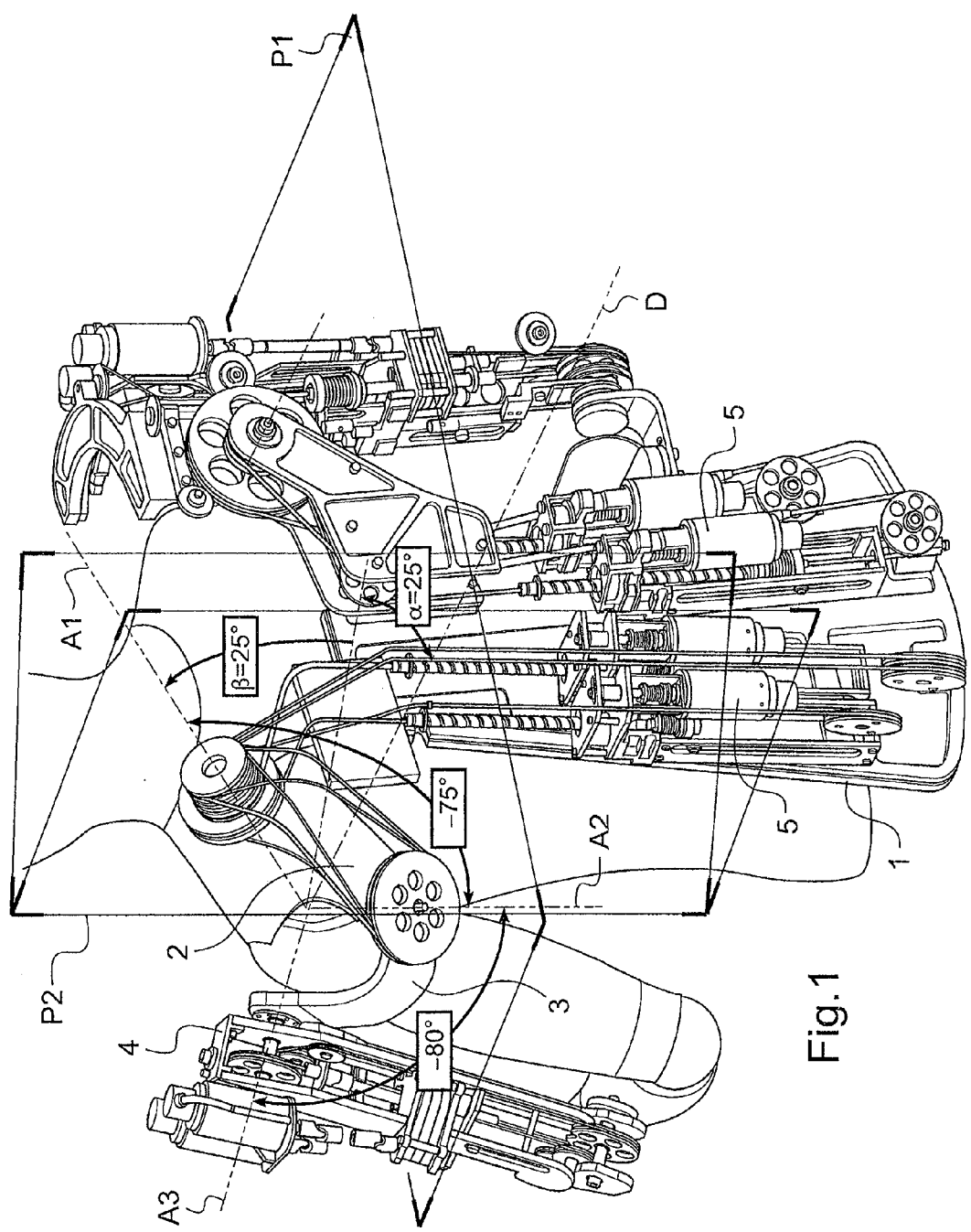
FIG. 1 is a perspective view from behind of a user wearing an orthosis provided with a shoulder mechanism in a particular embodiment of the invention.
Figure 2:
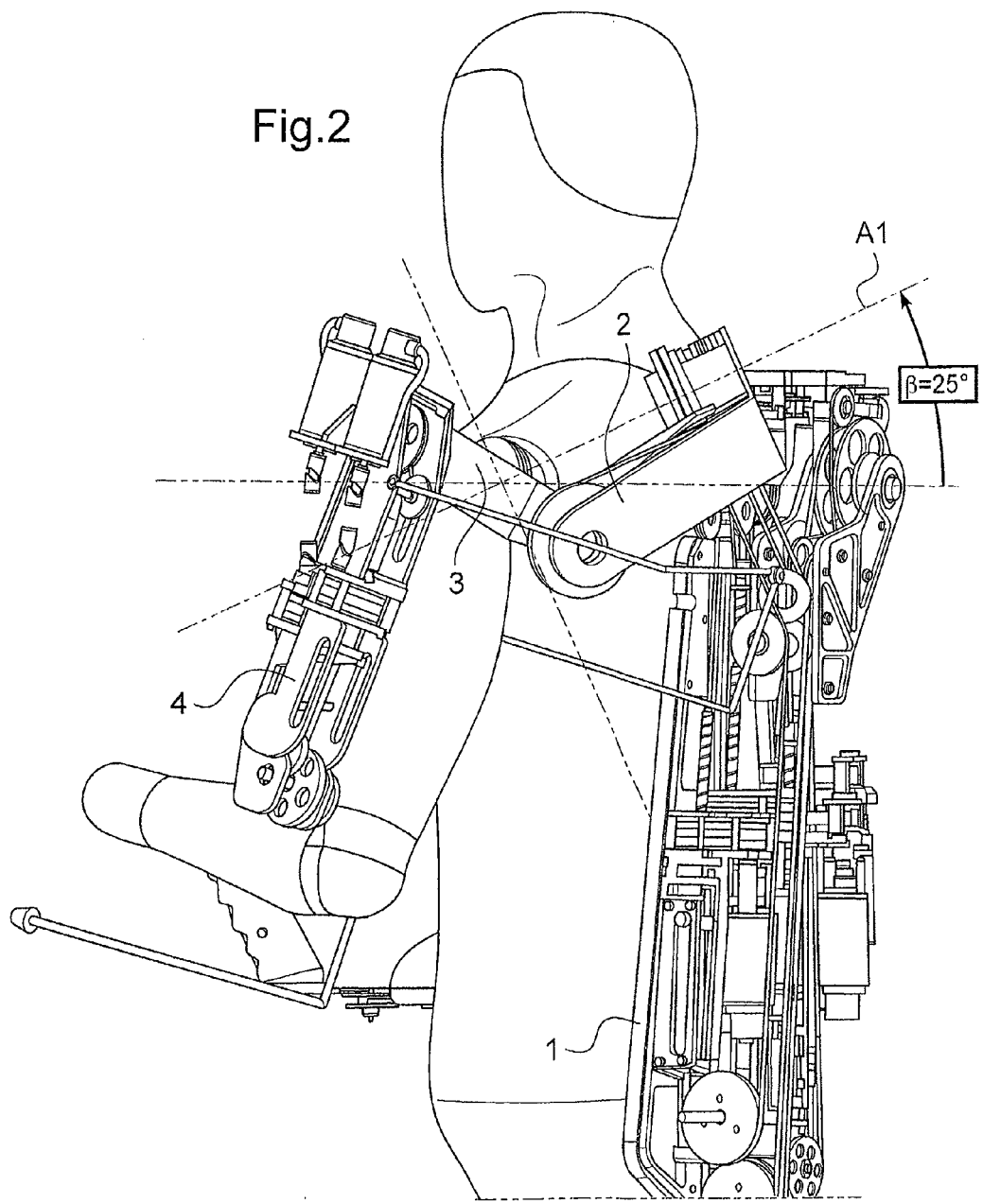
FIG. 2 is a perspective view of the same user, still from behind but closer to a side view.
Figure 3:
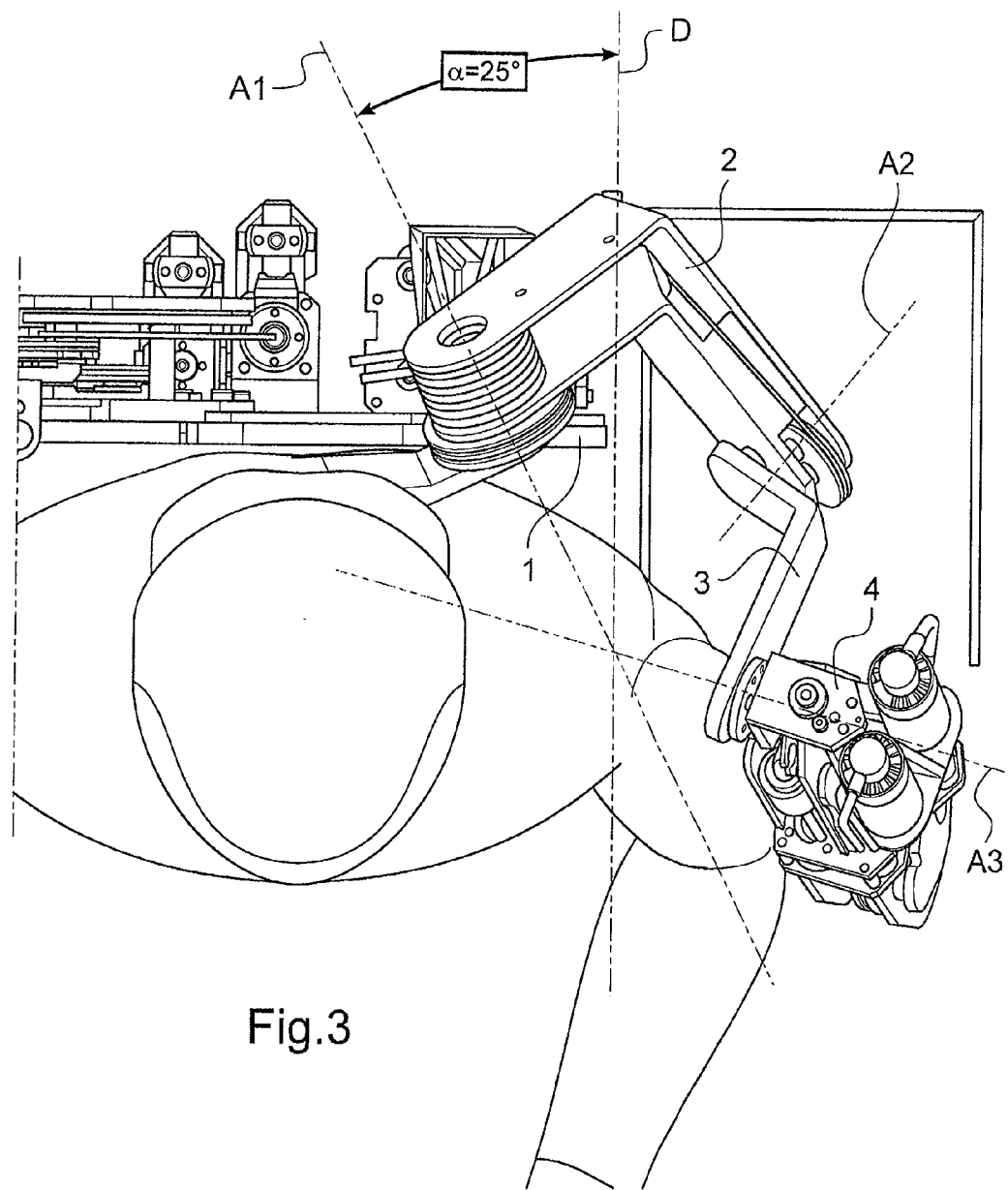
FIG. 3 is a plan view of the same user.

The shoulder mechanism shown in the figures comprises firstly a first element 1 or back piece that is shown here being worn directly by the user, and that extends over the user's back. The first element 1 has a second element 2 hinged thereto about a first hinge axis A1. According to the invention, the hinge axis A1 is inclined as follows. Let P1 be a horizontal plane containing the center of the shoulder, and D a longitudinal direction in the plane P and extending from front to back relative to the user, then the hinge axis A1 is at an angle $\alpha$ of 25 degrees in the plane P1 (which angle can be seen lifesize in FIG. 3), and at an angle $\beta$ of 25 degrees relative to a horizontal in a vertical plane P2 (which angle can be seen lifesize in FIG. 2).

Then a third element 3 is hinged to the second element about a second hinge axis A2 that is oriented at an angle $\gamma$ of 75 degrees relative to the first hinge axis A1.

Finally, the upper arm 4 of the orthosis is hinged to the third element about a third hinge axis A3 that extends at an angle of 80 degrees relative to the second hinge axis A2. Thus, and according to an essential characteristic of the invention, the three hinge axes extend in directions that define a non-orthogonal frame of reference.

The three hinges are embodied in this example by pivoting connections made using pivot bearings.

The three hinge axes coincide at a point that is the presumed center of the user's shoulder. However this arrangement is not essential in the context of the invention, and it is possible for the three hinge axes merely to converge in the vicinity of the presumed center without strictly coinciding therewith.

These arrangements enable the upper arm to move extensively without using circular slideways.

Actuating the degrees of freedom in pivoting about the first and second hinge axes is preferably performed with the help of cable actuators 5 fastened to the back piece 1 and having their cables received or deflected as required by pulleys mounted concentrically with the various hinges.

The invention is naturally not limited to the above description. In particular, the angle values are given by way of indication and may be adapted to the morphology of the user. A range of plus or minus 10 degrees about the values indicated suffices to accommodate most shoulder morphologies.

The invention claimed is:

1. A shoulder mechanism for an orthosis consisting essentially of in succession:
    a first element (1) that is stationary relative to a user;
    a second element (2) that is hinged to the first element about a first hinge axis (A1);
    a third element (3) having a first end carrying a hinge that hinges the third element to the second element about a second hinge axis (A2) and having a second end with a hinge that directly hinges the third element to an upper arm (4) about a third hinge axis (A3); and
    actuators that actuates the hinges;
    wherein the first, second and third hinge axes (A1, A2, A3) extending in directions that define a frame of reference that is non-orthogonal;
    wherein, when an arm of the user is at rest, the first hinge axis (A1) extends at a first angle ($\alpha$) in a range of plus or minus 10 degrees about an angle of 25 degrees in a horizontal plane containing a presumed center of the shoulder and relative to a longitudinal direction in said horizontal plane, the longitudinal direction (D) lying in the horizontal plane and extending from front to back relative to the user, and the first hinge axis (A1) extends at a second angle ($\beta$) in a range of plus or minus 10 degrees about an angle of 25 degrees in a vertical plane relative to the horizontal plane.

2. A shoulder mechanism for an orthosis according to claim 1, wherein the second hinge axis (A2) extends at a third angle ($\gamma$) in a range of plus or minus 10 degrees about an angle of 75 degrees relative to the first hinge axis (A1).

3. A shoulder mechanism for an orthosis according to claim 2, wherein the third hinge axis (A3) extends at a fourth angle in a range of plus or minus 10 degrees about an angle of 80 degrees relative to the second hinge axis (A2).

4. A shoulder mechanism for an orthosis according to claim 1, wherein the first, second and third hinges are embodied by pivot bearings.

5. The shoulder mechanism for an orthosis according to claim 1, wherein the arm of the user is at rest when the upper arm is in the adducted position.

* * * * *